US009885647B2

(12) United States Patent
Grubb et al.

(10) Patent No.: US 9,885,647 B2
(45) Date of Patent: Feb. 6, 2018

(54) SEMI-DYNAMIC LEACH TEST DEVICE AND METHODS OF MAKING AND USING

(71) Applicant: CH2M HILL, Inc., Englewood, CO (US)

(72) Inventors: Dennis G. Grubb, Lansdale, PA (US); Dusty R. V. Berggren, Corvallis, OR (US); Anthony Dalton-Atha, Corvallis, OR (US)

(73) Assignee: CH2M HILL, INC., Englewood, CO (US)

( * ) Notice: Subject to any disclaimer, the term of this patent is extended or adjusted under 35 U.S.C. 154(b) by 140 days.

(21) Appl. No.: 14/682,862

(22) Filed: Apr. 9, 2015

(65) Prior Publication Data

US 2015/0290647 A1    Oct. 15, 2015

Related U.S. Application Data

(60) Provisional application No. 61/978,365, filed on Apr. 11, 2014.

(51) Int. Cl.
| | |
|---|---|
| *G01N 21/75* | (2006.01) |
| *G01N 13/00* | (2006.01) |
| *G01N 33/24* | (2006.01) |
| *G01N 1/10* | (2006.01) |
| *G01N 1/28* | (2006.01) |

(52) U.S. Cl.
CPC ............. *G01N 13/00* (2013.01); *G01N 33/24* (2013.01); *G01N 2001/1037* (2013.01); *G01N 2001/2826* (2013.01); *G01N 2013/003* (2013.01); *G01N 2013/006* (2013.01)

(58) Field of Classification Search
CPC .. G01N 13/00; G01N 33/24; G01N 2013/006; G01N 2001/2826; G01N 2013/003; G01N 2001/1037

See application file for complete search history.

(56) References Cited

U.S. PATENT DOCUMENTS

| 7,930,948 B2 | 4/2011 | Shor et al. | |
|---|---|---|---|
| 2009/0193880 A1* | 8/2009 | Halverson | G01N 1/18 73/64.56 |

OTHER PUBLICATIONS

Dermatas et al, "An Evaluation of Arsenic Release from Monolithic Solids Using a Modified Semi-Dynamic Leaching Test" Journal of Hazardous Materials B116 (2004) 25-38.*
U.S. E.P.A. Method 1315, Mass Transfer Rates of Constituents in Monolithic or Compacted Granular Materials Using a Semi-Dynamic Tank Leaching Procedure, Rev. 0, Jan. 2013.
Matko, Larry. "Use of a Commercially Available Polyethylene Bag as an Absorptive Medium for Semi-volatile PAH Analysis," Second Annual RE3 Conference in Philadelphia, PA. Jan. 29, 2014.

* cited by examiner

*Primary Examiner* — Dennis White
(74) *Attorney, Agent, or Firm* — Dorsey & Whitney LLP (57) ABSTRACT

Disclosed herein is an insert device for semi-dynamic leach testing, the insert device including a support and an absorptive polymer disposed on the support, the insert device characterized by a sheet-like form having a first and second major side. The device is useful in testing of both radial and unidirectional leaching of organic compounds into water from solid samples.

18 Claims, 7 Drawing Sheets

SEMI-DYNAMIC LEACH TEST DEVICE AND METHODS OF MAKING AND USING

CROSS REFERENCE TO RELATED APPLICATIONS

This application claims the benefit of priority pursuant to 35 U.S.C. § 119(e) of U.S. provisional application No. 61/978,365 filed 11 Apr. 2014 entitled "Semi-dynamic leach test device and methods of making and using," which is hereby incorporated herein by reference in its entirety.

TECHNICAL FIELD

This disclosure relates to devices and methods for absorbing leachates from water.

BACKGROUND

Diffusion testing of solid samples (e.g. U.S. E.P.A. Method 1315, Mass Transfer Rates of Constituents in Monolithic or Compacted Granular Materials Using a Semi-Dynamic Tank Leaching Procedure, Rev. 0, January 2013 and it predecessors) is traditionally accomplished by immersing a sample in a bath of deionized water, allowing a period of time to pass, collecting the water, replacing it with fresh water, and repeating these steps over numerous specified leaching intervals, typically up to total duration of 63 to 90 days. The collected water is subsequently tested for the presence of inorganic/organic compounds. EPA Method 1315 describes two main configurations for semi-dynamic leach (SDL) testing: 1) radial mass transfer from monolithic and solidified cylinder samples positioned in the center of a water bath (radial SDL test); and, 2) one-dimensional (1-D) mass transfer from the top exposed planar surface of a soil or soil-like media compacted in a cylindrical mold into an overlying water column (1-D SDL test).

Radial SDL tests are typically conducted in large glass jars, for example a 2 liter jar or larger, wherein the sample to be tested is suspended in the center of the jar using a wire or string, or by placing it on a porous mesh pedestal or housing. The jar is then filled with water, then repeatedly exchanged out at the end of each leaching interval. Unidirectional, or 1-D SDL tests may be conducted using a compacted soil or soil-like sample in an open-faced mold that can be placed with a snug fit in the bottom of a cylindrical water bath.

The exchangeable water bath of the SDL test aids in the quantification of leaching rates of various compounds from solids such as soil, sediments, ash materials, cemented media, industrial byproducts, waste media, building materials, and the like, and semi-solid materials such as mine tailings, pastes, gels, tarry wastes, hydrated clays and sludges, drilling muds and the like. However, many sparingly soluble organic compounds may reach their effective saturations in the water bath during a given leaching interval, especially long testing intervals (>2 days). Mass transfer (diffusion or leaching) of these compounds can be greatly diminished or terminated as individual organic compounds approach their effective saturation in the water bath prior to change out.

U.S. Pat. No. 7,930,948 discloses the use of "gel elastomers" coated on the inside wall of jars used for the conventional tests, wherein the gel elastomers are capable of absorbing and retaining the leached compound(s). The positioning of the gel elastomer on the inside surface of the jar facilitates the establishment of a uniform gradient field for diffusion. Polydimethylsiloxane (PDMS) is one example of the gel elastomer. From a fabrication and deployment perspective, the gel elastomer is typically deposited inside the jar as a liquid (uncured) elastomer. The jar is then continuously rotated to create a uniform layer of the elastomer on the inner walls of the jar while curing. With heating, the curing process can take 60 minutes per jar. This fabrication process is cumbersome, time consuming, and an inefficient means to manufacture when a large number of such testing jars.

The gel elastomer is described as providing sufficient capacity to absorb the totality of leaching organic compounds, such that the water bath concentration of each organic compound is maintained at low levels, providing a strong gradient for mass transfer during each leaching interval of the test. In U.S. Pat. No. 7,930,948, the solid phase sample (cylinder/compacted soil) is carefully removed after each leaching interval and placed in a new water bath within a jar having its internal walls coated with PDMS, thus commencing the next leaching interval. The accumulation of organic compounds in both the water bath (eluate) and the gel elastomer (PDMS) liner within the jar used in the previous leaching interval is then measured. The water bath is removed in its entirety for analysis, allowing the PDMS within the jar to be extracted with a fixed amount of solvent to recover the absorbed compounds from the gel elastomer matrix. The solvent is then analyzed for the organic compound(s) of interest.

The gel elastomer coating described in U.S. Pat. No. 7,930,948 is cured on the inside wall of the jar, therefore, it is not removable and limits each jar to a single use. It may only be used for one leaching interval and extraction with one solvent, which limits the analytical work that can be performed with one lined jar. In the case of volatile organic compounds (VOCs), methanol is the preferred extractant for the gel elastomer jar liner. For semi-volatile organic compounds (SVOCs) and pesticides, acetonitrile is the preferred extractant for the gel elastomer jar liner. Accordingly, the simultaneous analysis of different classes of organic compounds from a single gel elastomer jar liner is precluded; multiple solid samples must be tested in parallel (duplicate) if the leaching of both VOCs and SVOCs from the same solid phase sample is required, effectively doubling the materials testing cost.

Subsequent solvent extraction requires the coated jar to be contacted with a known quantity of extractant (solvent), requiring that either the entire jar is filled with solvent, or a lesser quantity be added, which requires rotating the jar to ensure adequate contact of the solvent with all of the gel elastomer. Moreover, multiple solvent extractions of the gel elastomer may be required to remove the entire absorbed mass of organic compounds.

Finally, it is difficult to determine that the amount of gel elastomer in the jar is sufficient for the test; that is, whether sufficient capacity is provided by the amount of thin gel elastomer coating on the jar. Making very thick coatings of gel elastomer on the jar is inefficient and adds to the unit cost of the SDL test.

TestAmerica Laboratories, Inc. of Darien, Conn. made a presentation on Jan. 29, 2014 at the Second Annual RE3 Conference (Philadelphia, Pa.) entitled "*Use of a Commercially Available Polyethylene Bag as an Absorptive Medium for Semi-volatile PAH Analysis*", describing a method wherein commercially available zip-top polyethylene bags are inserted into glass jars with the open top portion of the bag protruding from the jar. The solid sample is suspended within the jar and further within the bag, and the bag is filled with water. The bag is employed as the absorptive medium in the radial mass transfer of organic contaminants from the sample. It will be appreciated that this approach solves some of the problems associated with U.S. Pat. No. 7,930,948 discussed above.

However, since the entire polyethylene bag is not immersed in the water, it can be difficult to know the mass of the actual absorptive medium exposed to the water, which in turn makes quantification of leachate concentrations difficult. Additionally, the amount of total polyethylene mass available for absorption of organic compounds may not be sufficient in some cases, since commercially available bags are relatively thin, typically 2 mils (51 µm). Where insufficient mass is provided and saturation of the absorptive medium is reached, radial mass transfer stops until the bag is changed.

SUMMARY

Disclosed herein is an insert device for an SDL test device, the insert device including a support and an absorptive polymer disposed on the support, the insert device characterized by a sheet-like form having a first and second major side. In some embodiments, the support is fiberglass fabric and the absorptive polymer is a polydiorganosiloxane. The insert device is removable, exchangeable, and easily positionable within the interior of the test device.

Also disclosed herein is a method of making an insert device for an SDL test, the insert device including a support and an absorptive polymer disposed on the support and characterized by a sheet-like form having a first and second major side. In embodiments, the method includes a batch or continuous manufacturing process. In a continuous manufacturing process, the method includes unrolling a support and applying it as a web backing in a web-based process, applying a liquid absorptive polymer to the backing, solidifying the absorptive polymer by freezing, drying, or curing to form the insert device, and winding the insert device into roll form. In some embodiments, the method further includes unwinding at least a portion of the insert device roll and dividing the insert device into one or more portions sized for use in one or more SDL tests.

Also disclosed herein is a radial SDL test device including a container having a substantially cylindrical shape including an inner cylindrical wall and an opening; and an insert device including a support and an absorptive polymer disposed on the support and characterized by a sheet-like form having a first and second major side, wherein one major side of the insert device is disposed substantially in contact with the inner cylindrical wall of the container. In some embodiments the container is a glass jar.

Also disclosed herein is a 1-D SDL test device including a container having an opening; a lid designed to cover the container; and an insert device including an absorptive polymer disposed on the support and characterized by a sheet-like form having a first and second major side, wherein when the lid covers the container, the insert device extends across the opening and between the lid and the container such that one major side of the insert faces the interior of the container.

Also disclosed herein is an SDL test method including inserting an insert device into a container, the container having a substantially cylindrical shape including an inner cylindrical wall and an opening, the insert device including a support and an absorptive polymer disposed on the support and characterized by a sheet-like form having a first and second major side, wherein the inserting includes urging one major side of the insert device to contact the inner cylindrical wall of the container; adding a test sample and water to the container wherein the sample is immersed in the water; waiting for a period of time; removing at least the insert device from the container after the period of time; and extracting at least a portion of the insert device with a non-aqueous solvent. In some embodiments, the insert device is immersed in the water. In some embodiments, the water and sample are also removed after the period of time, and the jar is cleaned and reused in another SDL test. In some embodiments, after removing the insert device from the container, the insert device is divided into two or more pieces, and the two or more pieces are subjected to extraction using two or more different solvents.

Also disclosed herein is an SDL test method including adding a test sample to a container, the container having an opening and a lid designed to cover the opening, wherein the test sample is placed in the bottom of the container and substantially fills a bottom portion thereof; adding water to the container, wherein the water fills the container substantially to the top thereof; placing an insert device across the top of the container, the insert device including a support and an absorptive polymer disposed on the support and characterized by a sheet-like form having a first and second major side, wherein one major side of the insert device is in substantial contact with the water; placing the lid onto the container to affix the insert device in place; waiting for a period of time; removing at least the lid and insert device from the container after the period of time; and extracting at least a portion of the insert device with a non-aqueous solvent. In some embodiments, the insert device is disposed substantially within the lid and the lid and insert device are contemporaneously placed on the top of the container. In some embodiments, the water and sample are also removed after the period of time, and the container is cleaned and reused in another SDL test. In some embodiments, after removing the insert device from the container, the insert device is divided into two or more pieces, and the two or more pieces are subjected to extraction using two or more different solvents.

DETAILED DESCRIPTION

Disclosed herein are SDL test devices and methods of making and using the devices for absorbing and extraction of organic leachates. The leachates leach from solid samples into water, and the device is disposed within the water to absorb the leachates. The device is then removed from the water and the leachates are extracted using a non-aqueous solvent. The devices enable quantification or calculation of mass transfer potential of the leachates from a sample. The devices have several advantages that will be described below.

Definitions

As used herein, "SDL" means semi-dynamic leach; the term SDL is applied to mean an SDL test, SDL testing, or an SDL device, in context. An SDL test is unidirectional, or "1-D" in some embodiments, radial in some embodiments, or both as determined by context.

As used herein, the term "insert device" means a support and an absorptive polymer disposed on the support. The insert device is an SDL device and is employed in SDL test devices to carry out SDL tests.

As used herein, the term "absorptive polymer" means a thermoplastic or thermoset polymer that is capable of absorbing one or more organic compounds when contacted with water containing the one or more organic compounds, and is further capable of releasing the one or more organic compounds upon subsequent contact with a non-aqueous solvent, or extractant. The absorptive polymer is an elastomer in some embodiments. The absorptive polymer is synthetic in some embodiments.

As used herein, the term "support" means a film, porous film, perforated film, sheet, expanded sheet, perforated sheeting, mesh, scrim, screen, woven fabric, nonwoven fabric, and the like formed form a natural or synthetic polymer, metal, fiberglass, or mixture of two or more thereof, wherein the support is capable of receiving and retaining an absorptive polymer during assembly, storage, SDL testing, and extraction. In some embodiments, the absorptive polymer is applied to the support by applying a flowable polymer to the support followed by curing or solidification.

As used herein, the term "test device" means an insert device disposed within a container. The test device is an SDL test device.

As used herein, the term "container" means a receptacle capable of holding an insert device, a solid or semi-solid sample, and water in a manner that allows for radial or unidirectional mass transfer of leachates from the sample to the insert device.

As used herein, the term "sample", "solid sample" "semi-solid sample" or "test sample" means a solid or semi-solid material, as determined by context, wherein the material contains organic compounds that are capable of leaching into water over a selected period of time. A solid sample is divided in some embodiments, such as soil, sand, gravel, or the like; or monolithic, such as concrete, asphalt, or rock samples. A semi-solid sample is divided in some embodiments, such as mine tailings, muds, pastes, gels, creams, foams, high liquid content sediments, clays, sludges, tarry materials, or the like. The test sample is divided at least to the extent that it fits into a container suitable for an SDL test and is capable of being retained therein in a manner that allows for radial or unidirectional mass transfer of organic compounds in an SDL test.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Intended properties include, solely by way of non-limiting examples thereof, thickness, flexibility, partition coefficient, and absorptivity; intended positions include disposition of the insert device within the test device, or the sample within the test device. The effect on methods that are modified by "substantially" include the effects caused by any type or amount of materials in an insert device to one or more properties of absorptivity, or methods of SDL testing, wherein the manner or degree of the effect does not negate one or more intended properties or results; and like proximate considerations. Where modified by the term "substantially", the claims appended hereto include equivalents to these types and amounts of materials.

As used herein, the term "about" modifying, for example, the quantity of a material, process temperature, thickness, pressure, time period, and like values, and ranges thereof, employed in describing the embodiments of the disclosure, refers to variation in the numerical quantity that can occur, for example, through typical measuring and handling procedures used for making constructions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Insert Devices

Insert devices and methods of making them are described in this section. In embodiments, the inserts are formed for insertion in an SDL test device. In embodiments, insert devices include a support and an absorptive polymer disposed on the support. The insert devices are characterized by a sheet-like form, and have two major surfaces defining a thickness. The width and length dimensions of the sheet-like insert devices are not particularly limited. The sheets are suitably arranged in substantially planar form but are sufficiently flexible to be arranged, stored, or manipulated by a user into roll form, folded form, curved form, or the like.

The insert devices, including the support and the absorptive polymer materials, are selected by the user for both test performance and sufficient durability when subjected to the conditions of the SDL test as well as the subsequent extraction. In some embodiments, sufficient durability for testing of a broad range of test samples is imparted by the use of materials that are stable to exposure to water for long periods of time, such as 1 to 30 days, at pH of about 1 to 13. This pH range is characteristic of aggressive leaching environments such as acid tailings and petroleum tars at low pH to lime/cement stabilized media and red muds at high pH. However, it will be appreciated that some test samples contain one or more organic, inorganic, or organometallic compounds that are deleterious to some absorptive polymers, support materials, or both regardless of pH, or cause pH to lie outside the range of 1 to 13. Thus, sufficient durability in the SDL test means that the insert device construction is intact at the end of the SDL test, without substantial delamination; and that the absorptive polymer and support materials are not substantially degraded or dissolved at the end of the SDL test. The materials used to form the insert device are optimized for sufficient durability in a particular SDL test, that is, optimized for testing a selected sample.

The support is selected for disposition of an absorptive polymer thereon, wherein a targeted amount of the absorptive polymer is controllably applied and substantially retained thereon during storage, SDL testing, and subsequent solvent extraction. In some embodiments, the support provides increased surface area for contact between the absorptive polymer and the water during SDL testing when compared to a monolithic sheet of absorptive polymer. In embodiments where the absorptive polymer is cured after applying to the support, the support is selected to withstand the curing conditions, e.g. UV radiation, gamma radiation, heat, or the chemical reaction that occurs in presence of e.g. cure catalysts, high or low pH, and the like without undue degradation, and preferably without forming any measurable degradation products. In embodiments where the absorptive polymer is applied to the support by melting the polymer and flowing it onto the support, it is preferable that the support does not melt or undergo measurable degradation at the temperatures employed in achieving the melt application of absorptive polymer.

Supports suitable for use in forming the insert devices include films, sheets, meshes, screens, scrims, and porous or perforated sheets formed from polymers such as polyamides (nylons), acrylates, polyesters such as polyethylene terephthalate, polyolefins such as high density polyethylene or polypropylene, polyimides, polystyrene, acrylonitrile-butadiene-styrene, polyurethanes, polycarbonates, polyphenylene oxide, copolymers and blends thereof, and the like; sheets, meshes, screens, scrims, or perforated sheets formed from aluminum, tin, steel including stainless steel of various grades and galvanized steel, titanium, bronze, brass, copper, and the like, and include, for example, expanded metal, chain mail, hardware cloth, sintered metal mesh, and the like.

The ratio of open to closed areas of scrims, screens, meshes, perforated sheets, and the like are not particularly limited and vary according to the adhesive interaction between the support material and the absorptive polymer, desire for added surface area of contact between the absorptive polymer and the water in the SDL test, and desired volume or weight ratio of support to absorptive polymer.

In some embodiments, the support is a film that is embossed with a pattern, wherein the method of applying the absorptive polymer thereto effectively increases the surface area for contact between the absorptive polymer and the water in the SDL test while providing for the absorptive polymer to be disposed substantially only on one side of the support. In other embodiments, a two layer construction of support and absorptive polymer is embossed with a pattern on at least the absorptive polymer side in order to increase surface area for contact between the absorptive polymer and the water in the SDL test.

Suitable supports also include woven and nonwoven fabrics including fibers formed from glass, metals such as those listed above, or polymers such as those listed above. For example, nonwoven fabrics formed from polypropylene such as spunbond, nonwoven glass mats, and woven fiberglass cloths are usefully employed as supports to form the insert devices. Also useful are nonwoven polymer fabrics formed from bicomponent fibers, wherein a lower melting sheath covers a higher melting core, and the fibers are fused by heating a nonwoven mat of the fibers to a temperature between the two melt temperatures. Also useful as supports are various woven cloths, papers, and paper-like nonwovens formed from tree-based cellulose fibers, cotton fibers, and the like as well as blends thereof with synthetic fibers.

The support is characterized by an overall sheet-like form, that is, it has two major sides that define a thickness. The overall thickness of the support is not particularly limited but typically is between about 25 µm and 1 cm, typically about 50 µm to 5 mm or even about 100 µm to 3 mm. The overall thickness of the support will vary according to the selected material employed, and is determined by the ability to support the absorptive polymer during use as described below, and further to provide sufficient flexibility to be rolled up or folded, inserted into a container, unfurled within the container in a manner such that the insert device remains in contact with the sides of the container for the duration of the test, and finally removed intact from the container after a selected leaching interval.

In some embodiments, the support is further cut using a blade such as a box cutter, scissors, die cutter, and the like; in some such embodiments, the insert device (that is, the support with the polymer disposed thereon) is also conveniently cut using a blade.

In some embodiments, the support is also an absorptive polymer; that is, it is capable of absorbing one or more organic compounds when contacted with water containing the one or more organic compounds, and is further capable of releasing the one or more organic compounds upon subsequent contact with a non-aqueous solvent. Thus, for example, a film, nonwoven, screen, mesh, or scrim formed from polyolefin is likely also an absorptive polymer. In some embodiments, the support itself is useful as the absorptive polymer and no additional polymer is applied. In other embodiments, the support is a second absorptive polymer having different absorptive capabilities from the absorptive polymer. In some such embodiments, the absorptive polymer and the second absorptive polymer are usefully combined in the SDL test to provide greater absorptive capacity for samples having a range of compounds with variable solubilities, that is, where the partition coefficient of two or more organic compounds with respect to the two absorptive polymers is very different.

As will be seen from the methods of use outlined below, whether or not an additional polymer is applied thereto, the support itself is included in the subsequent quantification of organic compounds absorbed from the water in the leachate testing. Thus, additional absorptive capacity of the support is not deleterious to the testing and in some embodiments is beneficial where large amount of one or more organic components are present in a solid sample to be tested, or for testing of samples having a range of compounds with variable solubility properties.

Absorptive polymers suitable for use in forming the insert devices include thermoplastics and thermosets capable of absorbing one or more organic compounds when contacted with water containing the one or more organic compounds, and is further capable of releasing the one or more organic compounds upon subsequent contact with a non-aqueous solvent. In some embodiments the absorptive polymer is an elastomer. In some embodiments the absorptive polymer is synthetic.

Suitable absorptive thermoplastic polymers include hydrophobic synthetic polymers such as polyolefins including polyethylene, polypropylene, copolymers thereof, and copolymers thereof with 1-butene, 1-hexene, 1-octene, and the like; chlorinated olefinic polymers such as polyvinylchloride and polyvinylidenechloride; hydrophobic polyurethanes and polyesters; block copolymers of styrene and butadiene; hydrophobic acrylate homopolymers and copolymers including monomers such as n-butyl, iso-butyl, or t-butyl acrylate, n-octyl or iso-octyl acrylate, decyl acrylate, undecyl acrylate, dodecyl acrylate, and partially fluorinated analogs thereof as well as perfluorocarbon acrylates such as perfluorobutyl acrylate, perfluorooctyl acrylate, and the like; and butyl rubber (isobutylene-isoprene copolymers).

Where the absorptive polymer is a thermoplastic, in some embodiments it is applied to the support in molten form such as by extrusion coating, injection molding, and the like; in some embodiments, application of pressure such as by passing the combined support and molten polymer through a nip or under a hydraulic press is employed in order to fully embed the polymer within the support, where such embedding is desired. In other embodiments, the thermoplastic is applied by solution coating followed by evaporation of the solvent e.g. by heating. Solution coating is useful in embodiments for achieving a high penetration of e.g. fabrics by the polymer, or in some embodiments for achieving adhesion of the absorptive polymer to the support; however for very thick polymer layers such techniques are often impractical due to the long drying times required to ensure that no solvent contamination is present for the intended purposes of subsequent SDL testing.

In some embodiments a thermoplastic absorptive polymer is applied by polymerizing after application to the support. For example, acrylate polymers are suitably cured by thermal or radiation curing (UV radiation, gamma radiation, or electron beam) after application to a support. Polyurethanes are suitably polymerized after addition to a support by employing thermochemical means when a diisocyanate is applied in the presence of a diol. Other such combined application and polymerization and combined polymerization and cure schemes are easily envisioned by one of skill in the art.

Suitable absorptive thermoset polymers include polydiorganosiloxanes such as polydimethylsiloxane (PDMS), natural and synthetic crosslinked rubber, and crosslinked acrylate polymers including any of those listed above wherein a diacrylate, triacrylate, or tetraacrylate is included in the composition as it is applied to the support, followed by curing via actinic radiation as described above. Synthetic rubbers include styrene-butadiene rubber (SBR) and ethylene-propylene-diene (EPDM) rubbers wherein the diene component is dicyclopentadiene, ethylidene norbornene, or vinyl norbornene; in some embodiments the EPDM rubber is additionally cured using a peroxide to increase crosslink density.

Thermoset absorptive polymers are crosslinked after application to the support. For example, PDMS is typically applied to the support as a linear or cyclic, flowable polymer having a viscosity that ranges from water-like to a thick, honey-like syrup. Crosslinking mechanisms include $Bu_2Sn(OAc)_2$ catalyzed (acetoxy), Pt catalyzed (hydrosilylation), D3 ring-opening chain extension and cure, and radiation cure. Due to residuals that can affect testing outcomes, radiation cure or hydrosilylation is preferred over acetoxy cure. D3 ring opening is useful in embodiments where thick layers of PDMS are not required, since D3 (a cyclic siloxane oligomer) is a low viscosity material and thus achieving thick layers prior to chain extension is often not practical.

Figure 1A:
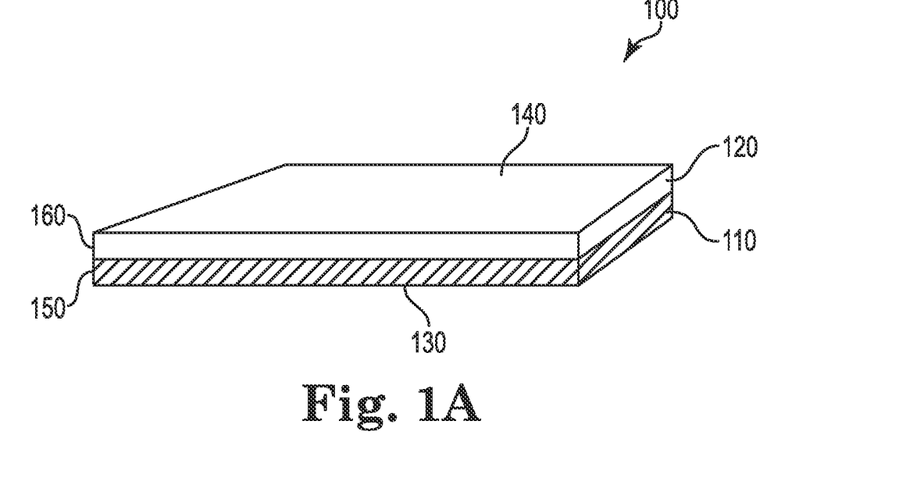
FIGS. 1A and 1B are schematic views of an insert device of the invention.
Figure 1B:
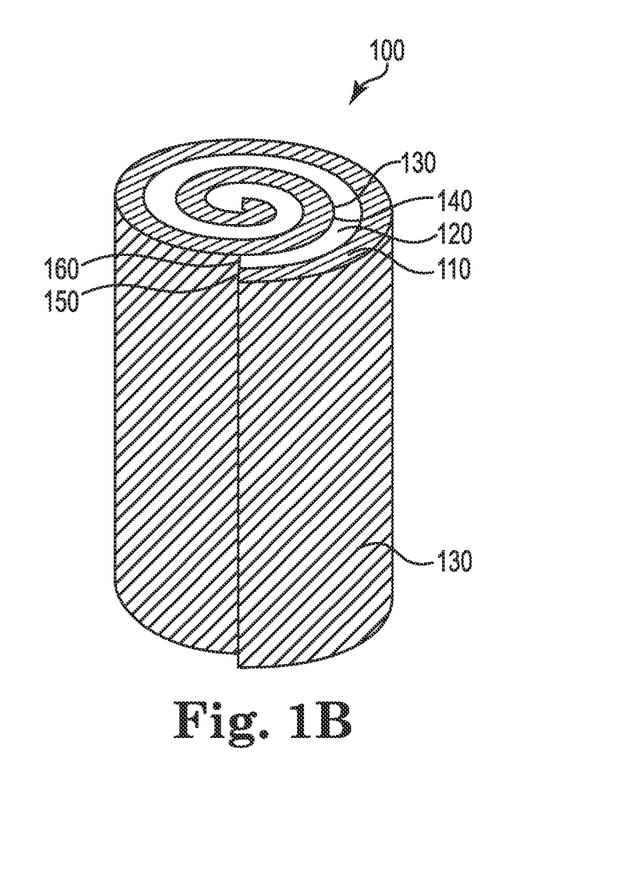

FIGS. 1A and 1B are schematic views of an insert device. FIG. 1A shows insert device 100 having support 110 that is a film with absorptive polymer 120 disposed thereon. Insert device 100 is characterized by a sheet-like form having a first major side 130 and second major side 140 and edge 150 describing a thickness 160. FIG. 1B shows insert device 100 in rolled form. First major side 130 formed from support 110 is disposed as the outer surface of the roll. Second major side 140 is disposed in contact with another section of the insert device first major side 130. Edge 150 describing thickness 160 is exposed at the outer side of the roll. It will be understood that FIGS. 1A and 1B are intended to show one representative embodiment of the indicated device, and many variations are possible based on the descriptions herein.

The insert devices are made using a method selected for the particular support and absorptive polymer combination. In one exemplary embodiment, PDMS is cured after applying to a fiberglass support. Thus, fiberglass cloth is coated with uncured PDMS base of dimethylvinyl terminated dimethyl siloxane that is mixed with a crosslinking agent, such as tetra(trimethylsiloxy)silane, in the presence of a catalyst such as Karstedt's catalyst or $H_2PtCl_6$; the mixture on the fiberglass is heated to cure the PDMS and form the insert device. The insert device can be folded, rolled, etc. for insertion into a test device.

In another embodiment, a nylon scrim support, in web form, is run through an extruder and a 2 mm bead of low-density polyethylene is extrusion coated onto the scrim; the coated scrim is passed through a nip to ensure a consistent coating thickness and further to embed the polyethylene uniformly throughout the scrim. In yet another embodiment, a 50 µm thick polyester film is die coated with a 1 mm thick coating of UV curable composition including n-butyl acrylate, isooctyl acrylate, dodecyl acrylate, hexanediol diacrylate, a prepolymerized mixture thereof, and a photoinitiator; the coated mixture is irradiated at a suitable wavelength for a suitable period of time to achieve a completely crosslinked hydrophobic coated polyester film.

In some embodiments, an absorptive polymer is coated on the first major side of the support, and a functional polymer is coated on the second side thereof (optionally employing the same application and/or curing methodology as used for the absorptive polymer). In some embodiments, the functional polymer is a second absorptive polymer. In some embodiments, the functional polymer is an absorptive polymer, but has an additional function other than absorption of organic compounds during an SDL test. In still other embodiments, the functional polymer is not absorptive of organic compounds and has a function other than absorption of organic compounds during an SDL test.

Examples of functions other than absorption of organic compounds include pressure sensitive adhesive functions, wherein the functional polymer adheres to the container wall; or indicator functions, such as a material that undergoes a visible appearance change in variable conditions of pH, temperature, or in the presence of undesirable contaminants that foul the SDL test, such as the presence of a threshold amount of fungi or bacteria. In some embodiments, the support is also a functional polymer.

In some embodiments the insert device includes a handle, string, wire, strap, clasp or other protrusion that is not absorptive of the organic compounds that leach from the solid sample. The protrusion is designed and adapted to assist the user in applying the insert device to the container, in holding the insert device in a selected position within the container, to remove the insert device from the container, to hold a sample or sample stage, or two or more thereof.

In some embodiments, the protrusion is simply a section of the support that does not include the absorptive polymer, and the dimensions of the insert device and protrusion are such that the protrusion protrudes above the level of the water during the SDL test while the absorptive polymer is completely immersed in the water during the test. In other embodiments, a wire, string, strap, or other protrusion is added to the combined support and absorptive polymer during the assembly of the insert device. For example, in some embodiments the protrusion is placed with a portion thereof disposed in contact with the support prior to extrusion coating of the absorptive polymer onto the support, wherein the solidification of the molten polymer serves to secure the protrusion within the insert device assembly. In other embodiments the protrusion is placed with a portion thereof disposed in contact with the support prior to applying a curable polymer to the support, wherein the curing of the polymer serves to secure the protrusion within the assembly; or some other means of securing the protrusion thereto.

In some embodiments, the protrusion is designed and adapted to assist the user in affixing the insert device within a container in a secured and repeatable fashion in order to provide consistency in placement of the insert device from one test device to another. In some such embodiments, the protrusion further traverses the support, optionally embedded within the absorptive polymer, across a length or width of the support to provide additional shaping, stiffness, or adhesion of the insert device within the test device. In other embodiments, the protrusion is designed to affix or hang over the opening of the container; in some such embodiments the protrusion is foldably conformable, such as a tin or aluminum member such as a strip or wire that is easily folded over the opening of the container and holds the insert device in a selected position within the container. In still other embodiments, the protrusion is designed and adapted to hold or suspend a solid sample within the test device during an SDL test.

In some embodiments, the insert device is provided with a liner on one or both major sides thereof during storage. In embodiments where the insert device is formed using a web-based process, a large amount of the insert device is suitably formed in one manufacturing run. The product of such manufacturing methods is capable of being stored for weeks, or months, or even years prior to use. Since the insert devices are suitably employed in quantitative analysis of small amounts of organic compounds, it is advantageous in some embodiments to provide a protective liner or layer on one or both major sides thereof to maintain cleanliness of the insert device, or protect it from environmental or incidental sources of oxidation, humidity, or UV radiation. Additionally, in some embodiments, the absorptive polymer has a tendency to block (adhere to itself) or has a high coefficient of friction and thus storage of the insert device in a roll format is inconvenient for handling; in such embodiments, disposing a liner on at least one major side thereof prevents such problems and eases handling.

Suitable liners are conventional materials known by those of skill in the art and include, for example, paper or coated paper, such as silicone or polyethylene coated paper, polyethylene films, polyester films, thin nonwoven fabrics, and the like.

Test Devices

Test devices including the insert devices are described in this section. Also described are methods of assembling a test device. The test devices include at least a container having an insert device disposed within the container. As used herein, "insert device" means either an insert device as assembled or a portion thereof divided from an assembled insert device as described above, as determined by context.

The containers useful in the test devices include those that are useful in SDL testing, further when employed in conjunction with the insert devices described above. In some embodiments the container has a substantially cylindrical shape to provide for consistent radial mass transfer toward the periphery thereof. While not limited to cylindrical shapes, in particular for unidirectional mass transfer, in many embodiments uniformity of mass transfer is provided by providing a cylindrically shaped container. Where a sample is rectangular, however, a rectangular container is usefully adapted to fit the sample in e.g. a unidirectional SDL test.

In embodiments the container is designed to hold a sample toward the bottom thereof to provide for consistent unidirectional (1-D) mass transfer toward the top thereof. In embodiments the arcuate inner wall of a cylindrical container is vertical or substantially vertical. The size of the containers is not particularly limited, and is selected for volume necessary to provide for effective radial or unidirectional mass transfer of substantially all of the selected organic compound(s) of interest from the solid sample to the absorptive polymer during the SDL test: sample size, expected concentration of organic compound(s) in the sample, amount of absorptive polymer in the insert device, and total water volume all contribute to this calculation.

In some embodiments, the volume of the container is selected to provide container volume to sample weight ratio, mL:g, of about 2:1 to 100:1, or about 2.5:1 to 80:1, or about 3:1 to 50:1, or about 5:1 to 25:1, or about 7:1 to 15:1. In some embodiments, the volume of the container is selected to provide a volume to sample surface area ratio, mL:cm$^2$, of about 0.5:1 to 20:1, or about 2:1 to 15:1, or about 5:1 to 12:1, or about 7:1 to 10:1. In some embodiments the container is a 2 liter glass jar; in some embodiments the container is a 1 liter cylindrical metal beaker; in still other embodiments, the container is a 5 gallon glass tank; larger and smaller containers are also useful in various embodiments of the test devices.

In embodiments, the inner surface of the container is not absorptive of the organic components that leach from the sample during the SDL testing. Glass and metals, such as stainless steel, are examples of suitable materials for such testing, although useful materials for the containers are not limited to these. In embodiments, the inner surface of the container is resistant to water swelling and is stable and resistant to chemical attack over all possible pH ranges and with respect to all expected leachates. In some embodiments, the container is a composite material such as a metal-lined plastic container. Where metal is employed as the inner surface of the container, the metal or oxidized versions of it should not be a source of dissolved metal molecules or ions, and the metal should not catalyze any reactions with the compounds that leach from the test sample. Where the container is not absorptive of the organic compounds that leach from one or more samples in the SDL tests, the containers are advantageously cleaned and re-used for one or more subsequent SDL tests.

In some embodiments, the test device is assembled by disposing the insert device within a container for radial mass transfer testing. In other embodiments, an insert device is placed between a container and a lid for unidirectional mass transfer testing. It is a feature of the invention that the insert devices are prepared easily and conveniently ahead of time, on any selected scale and by the selected means; easily stored in any amount and divided ahead of time or just before use by cutting or otherwise dividing out a selected and controlled amount of the insert device, and thus are easily added to the container to form the test device at the selected time. No special apparatus is required to assemble the test device; no special expertise is required to do so, and no extended period of time is required for the assembly. In embodiments the test device is assembled by folding or rolling the selected amount of the insert device and simply placing it inside the container.

It is a further feature of the invention that containers of a range of sizes are easily addressed by a single supply of the insert device. A selected size of insert device is easily formed in batch mode using a selected set of materials and methods. However, where the insert device is made in a web format, i.e. using a continuous web manufacturing method where the insert device is then stored in roll form, a selected width and length is easily divided from the web by cutting or slicing, followed by application to a container to form a test device. In this manner, the insert device portion is conveniently controlled for both weight and dimensions, providing for consistency between tests where needed. Continuous manufacturing further provides optional protrusions, liners, and the like with ease to the insert device constructions.

In some embodiments the insert device is applied substantially in contact with one or more interior surfaces of the container. For example, in a cylindrical container, the insert device is applied substantially in contact with at least a portion of the arcuate interior vertical wall. This configuration ensures that the radial diffusion field surrounding the monolithic sample is substantially uniform during the SDL test. In some embodiments, upon subsequent addition of water and the solid sample to the container having the insert device disposed therein, the insert device is completely immersed in the water. Efficient radial mass transfer of organic compounds leaching from the solid sample is incurred by placing the insert device in close proximity to, or substantially in contact with an inner wall of the container. Thus, in embodiments the support material and/or absorptive polymer material are further selected to work in conjunction with the container to allow the user to insert the insert device into the container in a convenient fashion, then apply the insert device against the walls of the container. In some embodiments, the container is at least partially filled with water prior to inserting the insert device; in other embodiments, the insert device is added to the container prior to adding water.

Figure 2:
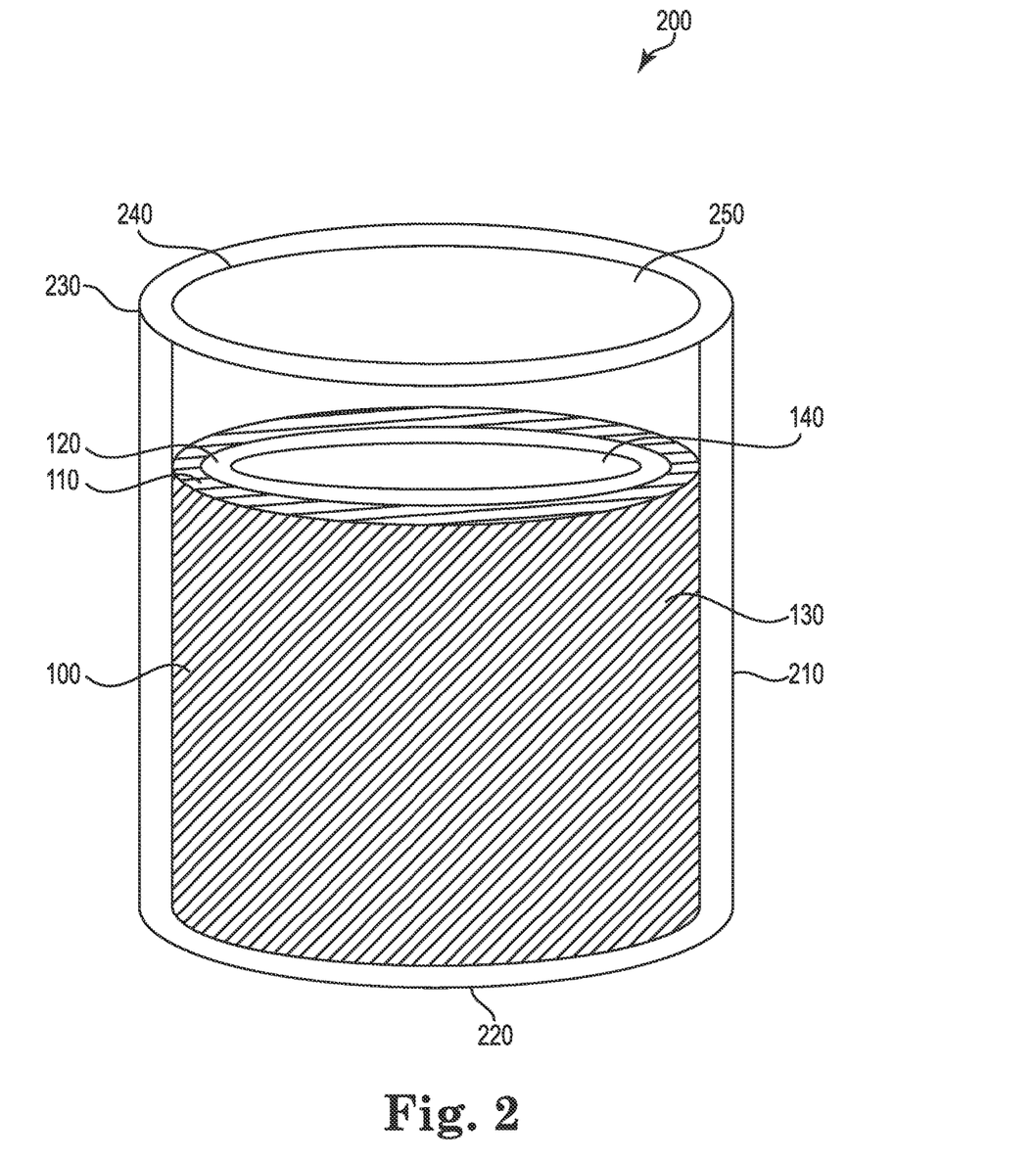
FIG. 2 is a schematic view of a radial SDL test device of the invention.

FIG. 2 is a schematic view of a radial test device of the invention. Test device 200 includes a cylindrical container 210 defined by a round floor 220, arcuate or cylindrical wall 230 having inner wall 240 defining the inner diameter of container 210, and opening 250. Disposed within container 210 is insert device 100. Support 110 and first major surface 130 of insert device 100 is positioned in contact with inner wall surface 240 of container 210. Absorptive polymer 120 and second major surface 140 of insert device 100 faces the interior of the container 210. It will be understood that FIG. 2 is intended to be one representative embodiment of the indicated device, and many variations are possible based on the descriptions herein.

In some embodiments where a test device is a radial test device, frictional forces, or attractive or adhesive forces are present between a container inner wall and the support, or the absorptive polymer, or both that serve to maintain the insert device in substantial contact with the inner wall. Thus, for example, where the absorptive polymer is PDMS and the container is a glass container, filling the container with water causes physicochemical attraction between the PDMS and the glass to retain the insert device against the periphery of the container. In other embodiments the absorptive polymer is an acrylate and adhesive forces similar to pressure sensitive adhesive compositions such as POST-IT® adhesive levels are incurred when the insert device is gently pressed against the side of the container and remains adhered during the SDL. In still other embodiments, a springlike "memory" of the insert device causes it to tend to unfurl after placement in the container, and this tendency causes the insert device to become disposed at the periphery of the container. Thus, for example, where the insert device includes a steel mesh support, the insert device is folded or rolled up for insertion into the container, then when released the mesh urges the insert device to unroll, causing its placement along the walls of a cylindrical container.

Where the test device is a unidirectional test device, frictional forces, or attractive or adhesive forces are present between a container lid and the support, or the absorptive polymer, or both that serve to maintain the insert device in substantial contact with the lid prior to attaching the lid to the container. However, it will be appreciated that in unidirectional test devices such physicochemical attractive forces are less important since the lid attachment to the container serves to fasten the insert device and hold it in place during testing.

In radial testing embodiments, a stage or other device is included in the container for holding and positioning a solid sample in the form of a monolithic cylinder therein. It is desirable for testing purposes that the solid sample be retained in the container close to the center thereof to allow for maximum radial mass transfer of organic compounds from the sample into the water and towards the insert device residing in close proximity to, or substantially in contact with an inner wall of the container. As such, a wire stage, sample cup, harness, or other means of holding the sample in place is suitably used. In some embodiments, a combination of braces and strings are employed. Such mechanisms and apparatuses are described elsewhere, for example see U.S. E.P.A. Method 1315, *Mass Transfer Rates of Constituents in Monolithic or Compacted Granular Materials Using a Semi-Dynamic Tank Leaching Procedure*, Rev. 0, January 2013, at FIGS. 1a and 2; also see U.S. Pat. No. 7,930,948 at FIG. 1. In some embodiments, a sample is usefully positioned within the test device by suspending the sample from a wire or string. Any of these stages or sample holders, as well as others easily envisioned by one of skill, are suitably employed as needed to dispose one or more samples within the test devices.

In some embodiments, in particular where the SDL test is a 1-D SDL test, a receptacle is further employed to hold the material in a centralized location. Thus, for loose or semi-solid samples, such as soil, sand, granular, and other soft and/or high liquid content samples, a sample cup is employed and the sample is compacted using conventional techniques. See e.g. U.S. E.P.A. Method 1315, *Mass Transfer Rates of Constituents in Monolithic or Compacted Granular Materials Using a Semi-Dynamic Tank Leaching Procedure*, Rev. 0, January 2013. Other conventional techniques are also usefully employed.

In some embodiments, a protrusion supplied by, and disposed with the assembly of, the insert device is useful for suspending a sample, or a sample holder, within the container once the test device is assembled. For example, where the protrusions are one or more wires extending from the insert device toward the opening at the top of the container, the one or more wires are useful to form hooks, or loops, or some other configuration that is useful to hang a sample or a sample holder therefrom. The sample is hung from the protrusions and is immersed in the water within the container during the SDL test.

Methods of Testing

Methods of SDL testing using the test devices, and subsequent solvent extraction, are described in this section.

SDL testing includes assembling a test device as described above, adding deionized, distilled or other specified water and a solid sample to the test device, wherein the amount of water is sufficient to cover the sample, and allowing a selected period of time to pass; then removing the insert device and testing it for the presence of one or more organic compounds. In some embodiments, a sample cup or stage is included to position the sample near the center of the container volume during the selected period of time, as is described above. In some embodiments, the water fully covers the insert device during the selected period of time. In some embodiments, the insert device includes one or more protrusions that protrude from the water during the SDL test.

Radial SDL testing includes inserting an insert device into a cylindrical container having an opening, adding a test sample and water to the container wherein the sample is immersed in the water and the insert device is at least partially immersed in the water; waiting for a period of time; removing at least the insert device from the container after the period of time; and extracting at least a portion of the insert device with a non-aqueous solvent. In some embodiments, the insert device is completely immersed in the water. In some embodiments, the container is further fitted with a lid after the insert device, water, and test sample are added. In some embodiments, the water and test sample are also removed after the period of time, and the jar is cleaned and reused in another SDL test. In some embodiments, after removing the insert device from the container, the insert device is divided into two or more pieces, and the two or more pieces are subjected to extraction using two or more different solvents.

Unidirectional SDL testing includes placing a test sample in the bottom portion of container, the container having a floor, one or more substantially vertical walls, an opening at the top thereof, and a lid designed to fasten to the opening, wherein the test sample substantially fills the bottom portion of the container; filling the remaining volume of the container with water; placing an insert device across the opening of the container wherein one major side of the insert device is in substantial contact with the water; fastening the lid to the container to affix the insert device in place; waiting for a period of time; removing at least the lid and insert device from the container after the period of time; and extracting at least a portion of the insert device with a non-aqueous solvent.

In some embodiments, the insert device is disposed substantially within the lid and the lid and insert device are contemporaneously affixed to the container. In some embodiments, the container is an arcuate cylindrical container. In some embodiments, the water and sample are also removed after the period of time, and the container is cleaned and reused in another SDL test. In some embodiments, after removing the insert device from the container, the insert device is divided into two or more pieces, and the two or more pieces are subjected to extraction using two or more different solvents.

Unidirectional SDL testing requires test samples that substantially fill the bottom portion of the container in which the test is carried out. "Substantially filling the bottom cup and portion of the container" means that the test sample extends substantially across the floor of a container and substantially uniformly up along a portion of the wall(s) thereof. Thus, in various embodiments, sampling apparatus is selected to take a core from a solid sample that is designed to fit in close contact with the inner diameter of a cylindrical test container or the inner dimensions of e.g. a rectangular shaped container. In other embodiments, a loose or semi-solid sample such as soil, sand, granular and other soft, high liquid content materials, and the like is compacted into a sample container that is designed to fit in close contact with the inner diameter of a cylindrical test container or the inner dimensions of e.g. a rectangular shaped container. Compacting techniques are well known to those of skill and conventional compacting techniques are usefully employed in connection with the test sample containers employed in one or more unidirectional SDL testing methods of the invention.

In embodiments, the unidirectional SDL testing samples extend substantially across the floor of a testing container and substantially uniformly up along at least 10%, and up to as much as 70% of the height of the walls of the container, in some embodiments about 30% to 50% of the height of the walls of the container. The remainder of the container volume is filled with water, up to the top edge thereof and even beyond that point in some embodiments, wherein the surface tension of water allows a convex water-container-air interface to form. The insert device is usefully disposed inside the lid of the container, for example cut into a circular shape that fits within the interior of the lid or is slightly larger than the lid interior; and the lid is placed on top of the container and affixed thereto. In other embodiments, the insert device is disposed directly on top of the container, and the lid is placed on top of the insert device and affixed to the container. In such embodiments the insert device is usefully cut to a size that is nominally larger than the dimensions of the container opening. In either embodiment, the insert device is disposed in substantial contact with the water and directly above the sample. The test is then carried out substantially as described elsewhere herein. The leaching direction will be substantially unidirectional, from the bottom or floor of the container toward the insert device disposed at the top of the test device.

Samples usefully tested for the presence and amount of one or more organic compounds in conjunction with the SDL tests (both unidirectional and radial) are not particularly limited, and are described elsewhere. See for example U.S. E.P.A. Method 1315, *Mass Transfer Rates of Constituents in Monolithic or Compacted Granular Materials Using a Semi-Dynamic Tank Leaching Procedure*, Rev. 0, January 2013. Any such samples usefully tested using the SDL testing described in this protocol are also usefully tested using SDL testing by employing the methods used herein. Soil, such as treated soils, building materials such as cement and concrete, various sediments and residues, ash materials, industrial, mine and nuclear wastes, slags, muds, gels, sludges are examples of commonly tested non-limiting solid and semi-solid sample types.

Figure 3:
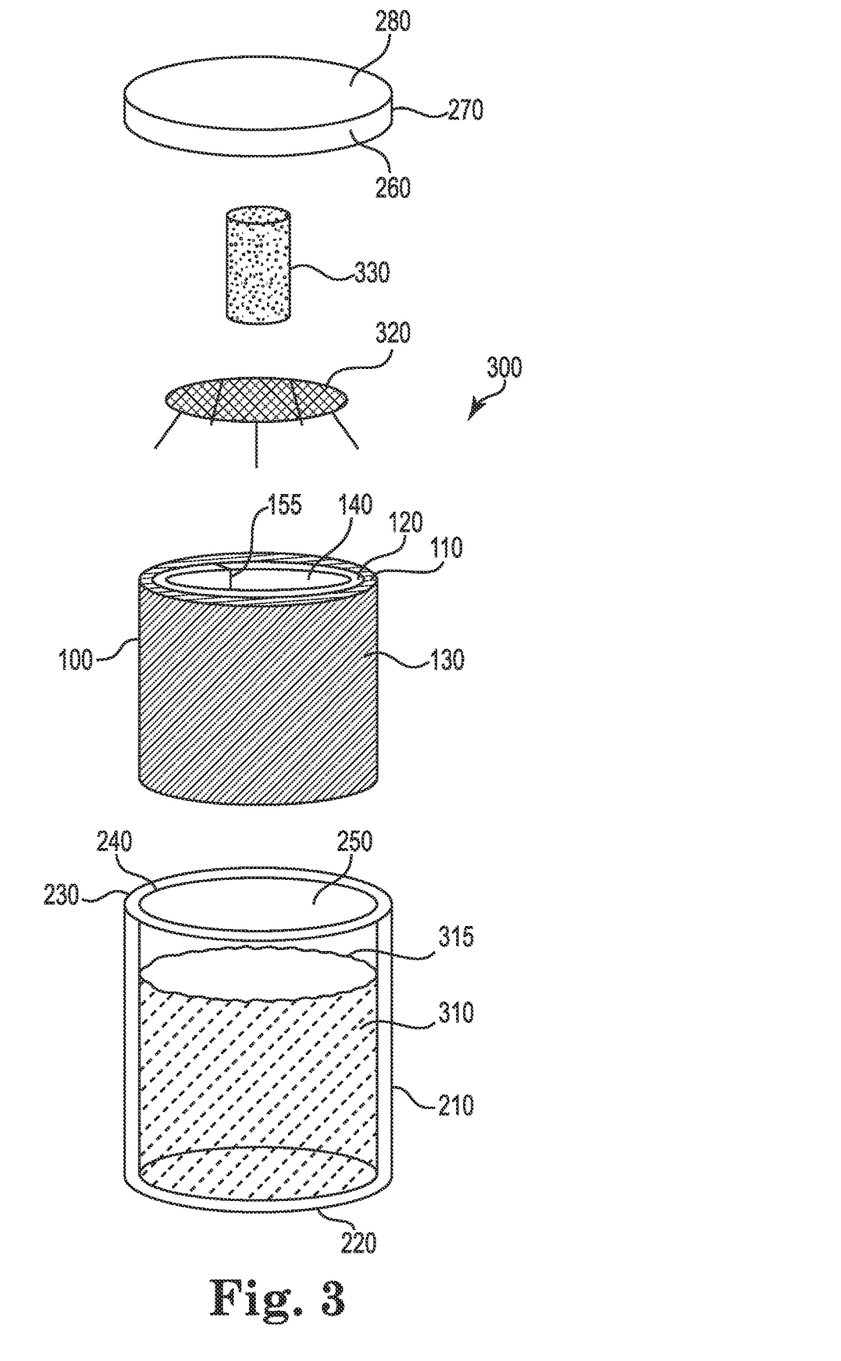
FIG. 3 is a semi-exploded view of a test device of the invention as used in a radial SDL test method of the invention.

FIG. 3 is an exploded view of a container loaded with water, an insert device, a sample, and a sample holder to form a radial SDL test assembly. Test assembly 300 includes cylindrical container 210 defined by a round floor 220, arcuate or cylindrical outer wall 230 and inner wall 240 defining the inner diameter of container 210, and opening 250. Container 210 is filled with water 310 to a selected level 315 that defines the surface of the water 310. Disposed within container 210 is insert device 100. Support 110 and first major surface 130 of insert device 100 is positioned to be in contact with inner wall surface 240 of container 210. Absorptive polymer 120 and second major surface 140 of insert device 100 is positioned to face the interior of the container 210. Sample stage 320 is positioned to be placed on floor 220 of container 210 and hold monolithic test sample 330, such that sample 330 is disposed near the center of the space defined by the second major surface 140, floor 220, and the surface of the water 315. Additionally, insert device 100 is wrapped so that edges thereof meet end-to-end 155. Container lid 260 is shown above container 210. Lid 260 is defined by cylindrical wall 270 and top 280. Lid 260 fastens across opening 250 of container 210, for example, by latches, pins, corresponding threaded grooves, snaps, tabs, matched o-ring and groove, and the like to seal container 210 and prevent escape of organic compounds that leach into the water 310. In some embodiments substantially no headspace (e.g. air pockets) remains in the container 210 once lid 260 is fastened thereto. It will be understood that FIG. 3 is intended to be one representative embodiment of the indicated assembly, and many variations are possible based on the descriptions herein.

Figure 4:
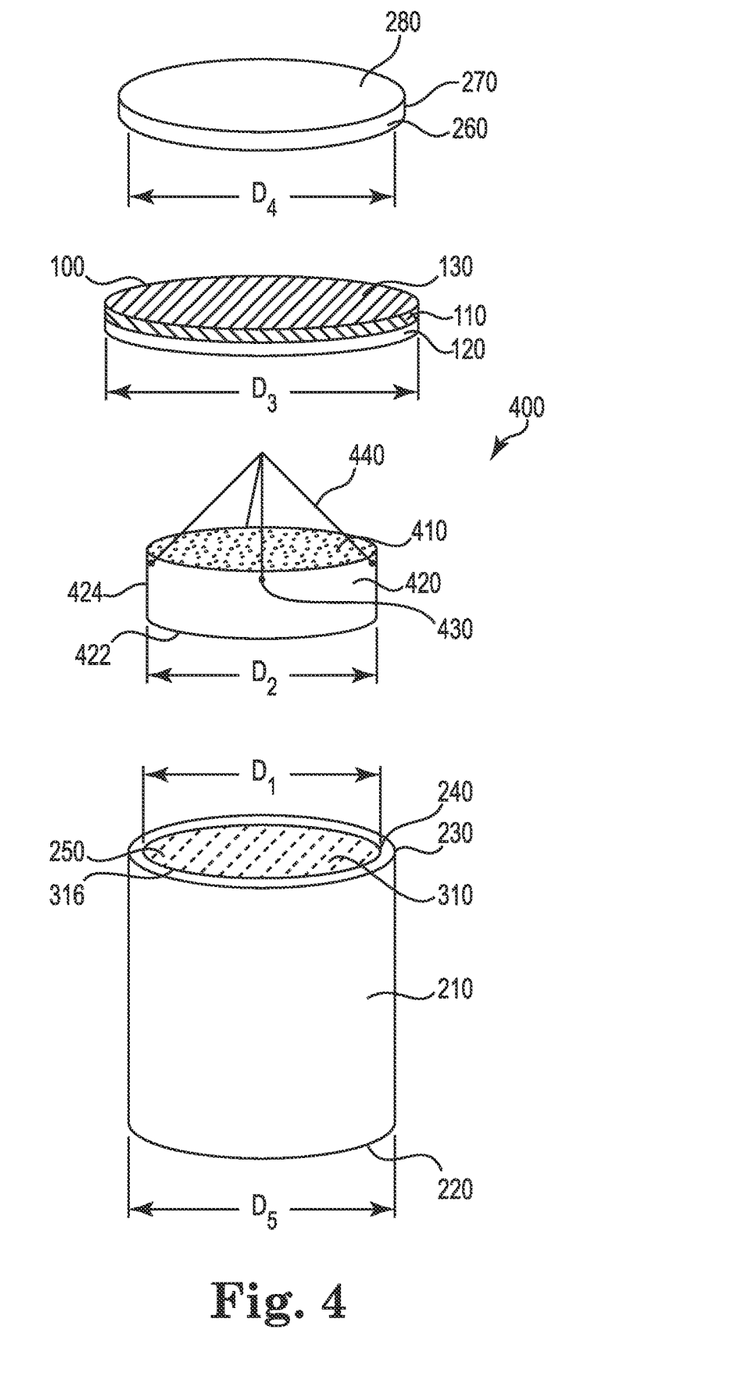
FIG. 4 is a semi-exploded view of a test device of the invention as used in a unidirectional SDL test method of the invention.

FIG. 4 is an exploded view of a container loaded with water, a sample, a sample holder, an insert device, and a lid to form a unidirectional SDL test assembly. Test assembly 400 includes cylindrical container 210 defined by a round floor 220, arcuate cylindrical outer wall 230 defining outer diameter $D_5$, inner wall 240 defining inner diameter $D_1$, and round opening 250. Container 210 is filled with water 310 to level 316 that corresponds to the level of opening 250. Test sample 410 is disposed within sample holder 420. Sample holder 420 is defined by round floor 422 and arcuate cylindrical outer wall 424 defining outer diameter $D_2$. Outer diameter $D_2$ is slightly less than inner diameter $D_1$ such that sample holder 420 fits slidably within container 210. Sample holder 420 has attachment points 430 for wires 440; wires 440 are usefully employed to lower and raise sample holder 420 into and out of container 210. When disposed inside container 210, sample holder 420 holding sample 410 extends substantially across floor 220 and at least about 30% of the height of walls 230, 240. Insert device 100 is cut to have diameter $D_3$, which is larger than diameter $D_1$ and in some embodiments larger than $D_5$. Insert device 100 is positioned to be disposed to extend across opening 250 of container 210, wherein absorptive polymer 120 is disposed in contact with water 310 at level 316. Container lid 260 is defined by cylindrical wall 270 having inner diameter $D_4$ and top 280. Inner diameter $D_4$ is defined by an inner wall of the lid that is not shown and is designed to fasten to outer diameter $D_5$ of container 210. Thus, lid 260 fastens to container 210, for example, by latches, pins, corresponding threaded grooves, snaps, tabs, matched o-ring and groove, and the like. Substantially no headspace (e.g. air) remains in the container 210 once lid 260 is fastened thereto. Insert device diameter $D_3$ is the same as $D_4$, or is larger than $D_4$. It will be understood that FIG. 4 is intended to be one representative embodiment of the indicated assembly, and many variations are possible based on the descriptions herein.

It is an advantage of the insert devices that if a large amount of leachate is observed in one or more samples, the insert devices are suitably changed for fresh insert devices during the test, and the insert devices combined at the completion of the leach test in a combined extraction for convenient quantification of even very large amounts of leachate present in a sample. As such, in the extraction tests described below, it will be understood that "insert device" means one or more insert devices, as required by the particular test and sample being tested.

At the conclusion of the SDL test, the insert device is loaded with one or more organic compounds. After the SDL test is terminated, the loaded insert device is removed from the container and subjected to one or more extractions or other testing protocols. "Extraction" as used herein means contact with a non-aqueous solvent or a blend of non-aqueous solvents; non-aqueous solvents include any solvent that is not water and is a liquid at about 20° C. The entirety of the loaded insert device from an SDL test is used, in some embodiments, in a single extraction. In other embodiments, the loaded insert device is cut, sliced, die cut, or otherwise divided into two or more pieces and each piece is subjected to a different extraction. Extraction is conducted by e.g. immersing the loaded insert device or a portion thereof in a jar with a selected solvent or solvent mixture and running multiple extractions which are combined, optionally concentrated, and tested for the presence of one or more organic compounds; or by running a Soxhlet type extraction followed by testing for the compound(s).

It is a feature of the invention that one SDL test can supply loaded insert device portions for two or more extractions. Since different organic compounds have different partition coefficients relative to the absorptive polymer (and/or the additional absorptive polymer, if the support is absorptive; or a functional polymer, if such is an absorptive polymer included as part of the insert device) in the presence of different solvents, it is understood by those of skill that a range of solvents or solvent blends are typically employed in extractions following SDL testing with absorptive polymers. The insert devices provide a method whereby a single SDL test provides loaded insert devices to supply two or more separate solvent extractions.

Additional Uses

Uses of the insert devices for applications other than leach testing are described in this section. Passive filtration applications suitably employ the insert devices, where trace amounts of leachate are encountered in water supplies. For example, residential swimming pools, personal drinking water supplies, and the like are applications wherein an insert device is suitably employed in contact with water to absorb small or trace amounts of organic impurities therefrom. The contact is, in various embodiments, completely passive such as standing water where an insert device is immersed in a hot water heater or a holding tank; or flow-by, such as an in-line whole-house water filter system where the insert device is provided in a flatbed or fluted conformation and water flows over it to provide for absorption of organic impurities from the water.

In another passive filtration application, an insert device is disposed as a liner surrounding farmland to scavenge excess organic nutrients, pesticides, herbicides, and the like from groundwater runoff or seepage and prevent the chemicals from reaching water supplies such as rivers, lakes, and aquifers.

In any of these embodiments, the loaded insert devices are suitably disposed after use, or are also useful for submission for subsequent testing. For example, a resident may wish to know the levels of one or more organic compounds in his or her drinking water; or a company may wish to test proper levels of application of a particular compound to e.g. farmland and determine when excess causes runoff of the chemical. In such cases, the individual or the company can use the loaded insert devices after passive filtration in one or more extraction tests to determine the amount of the one or more organic compounds in the loaded insert device.

Certain examples will now be set forth in the Experimental Section. The examples are not intended to be limiting and merely set forth some of the many possible embodiments for the appended claims.

EXAMPLES

The following materials are used in the Examples:

Small spreader. Plastic Bondo Spreader Model #357, SKU #451723 obtained from the Home Depot Inc. of Atlanta, Ga.

Fiberglass cloth. 14.6 cm×38.1 cm sections cut from Bondo part #20128 (obtained from the 3M Company of Maplewood, Minn.)

Polydimethylsiloxane (PDMS), SYLGARD®-184, 10:1 two-part mix obtained from DOW CORNING® Corporation of Midland, Mich.

Aluminum foil, food service grade, obtained from Reynolds Consumer Products Inc. of Lake Forest, Ill.

Glass Jar. 2 L straight walled, wide mouth clear jars, PN 170164, obtained from Scientific Specialties Service, Inc. of Hanover, Md.

Utility knife.

Wooden tongue depressor.

Plastic medicine cup, 30 mL, PN 22-66-470 obtained from Thermo Fisher Scientific Inc. of Waltham, Mass.

Example 1

A fiberglass cloth was unfolded and fine binding threads at the edge of the cloth were removed using scissors or a razor blade where necessary. The cloth was then refolded, wrapped in aluminum foil, and placed in a kiln set to 400° C. for about 4 hours, then removed and inspected for discoloration. The baked fiberglass was stored in a clean, sealed container until used.

The stored fiberglass cloth was removed from the sealed container and 14.6 cm×38.1 cm strips were cut from the cloth using a utility knife. A clean sheet of aluminum foil was laid on the work surface and a strip of fiberglass cloth was laid on the foil, wherein a margin of at least 3 cm of foil surrounded the cloth.

SYLGARD®-184 was blended at the indicated ratio using a wooden tongue depressor, and 30 mL of the mixed PDMS was dispensed into a 30 mL plastic medicine cup. The entire contents of the cut were emptied onto the cloth strip, using the tongue depressor to scrape the remnants from the cup. Then the spreader was used to evenly coat the cloth, scraping runoff back onto the cloth.

A second sheet of aluminum foil was used to cover the PDMS coated cloth, and this aluminum/coated cloth/aluminum construction was placed in an oven heated to 100° C. for about 10 minutes. Upon removal from the oven, one sheet of aluminum foil was peeled off, and the cloth was trimmed with a scissors to remove stray material at the edges. Then the remainder of the second aluminum strip was peeled off.

The resulting PDMS embedded fiberglass cloth is an Insert Device (ID) that can be used in a test device and employed in conjunction with a leach test method described herein.

Example 1C

PDMS coated jars were made in general accordance with the method of U.S. Pat. No. 7,930,948 (Examples section) except that 2 L jars were used and 28-30 g of PDMS per jar was used without degassing. The resulting coated jar is a Control Device (CD) that is used as a control test device in conjunction with some of the Control leach test methods (Control examples are denoted with "C") described herein.

Example 2

Radial semi-dynamic leach testing was carried out using the following procedure. An ID was formed according to the procedure of Example 1. The ID was weighed, then placed substantially around and in contact with the inner vertical wall of a 2 L glass jar such that the short side of the ID was vertically oriented. A solid sample was prepared for leach testing. A homogenized pesticide-impacted lagoon sample was solidified by adding cement to the sample and forming the mixture into a cylinder having a diameter of 5.08 cm and a length of 10.16 cm, for a surface area of 202.7 cm$^2$. The sample was secured using a harness and set on a stainless steel stage within the jar, in accordance with U.S. E.P.A. Method 1315, *Mass Transfer Rates of Constituents in Monolithic or Compacted Granular Materials Using a Semi-Dynamic Tank Leaching Procedure*, Rev. 0, January 2013, at Section 6.3.3. Then distilled water was added to fill the jar substantially to the top, and a lid was applied to seal the jar such that little to no headspace was included in the jar. A total of six sample and test device setups were prepared for side-by-side analysis.

At each of three intervals T3, T5, and T7 as shown in Table 1 below, defined in U.S. E.P.A. Method 1315 at Table 1 (p. 22), two samples were analyzed for the presence of α-hexachlorocyclohexane (α-HCH), a pesticide, in the eluate (water) and in the ID, and the averages of the analysis combined. First, the eluate was tested to determine the concentration of α-HCH using the protocol set forth in EPA Method 8081B, *Organochlorine Pesticides by Gas Chromatography*, Rev. 2, February 2007. The measured amount is the Eluate Concentration of α-HCH.

TABLE 1

Leach testing intervals. Reproduced from E.P.A. Method 1315, Table 1 (p. 22)

| Interval Label | Interval Duration (hr) | Interval Duration (days) | Cumulative Leaching Time (d) |
| --- | --- | --- | --- |
| T1 | 2.0 ± 0.25 | — | 0.08 |
| T2 | 23.0 ± 0.5 | — | 1.0 |
| T3 | 23.0 ± 0.5 | — | 2.0 |
| T4 | — | 5.0 ± 0.1 | 7.0 |
| T5 | — | 7.0 ± 0.1 | 14.0 |
| T6 | — | 14.0 ± 0.1 | 28.0 |
| T7 | — | 14.0 ± 0.1 | 42.0 |
| T8 | — | 7.0 ± 0.1 | 49.0 |
| T9 | — | 14.0 ± 0.1 | 63.0 |

Next, the ID was extracted with acetonitrile and the extractant tested for concentration of α-HCH. After removal of water and the sample from the jar, 30 mL of acetonitrile was added to the jar. The jar was capped and placed on rollers, and rolled for 16 hours at ambient temperature. Afterwards, the extractant was removed and tested by gas chromatography employing the methods set forth in protocol EPA Method 8081B, *Organochlorine Pesticides by Gas Chromatography*, Rev. 2, February 2007. The extraction was repeated four times with fresh acetonitrile, and each extractant tested for concentration to α-HCH. The combined amount of the four extractants was added, and the results were analyzed as follows:

Eluate concentration α-HCH*eluate volume α-HCH=total mass α-HCH in eluate;

Sum of 4 extracts*30 mL=total mass α-HCH adsorbed in PDMS.

(Total mass α-HCH adsorbed in PDMS+total mass α-HCH in eluate)/eluate volume α-HCH=effective α-HCH concentration.

Figure 5:
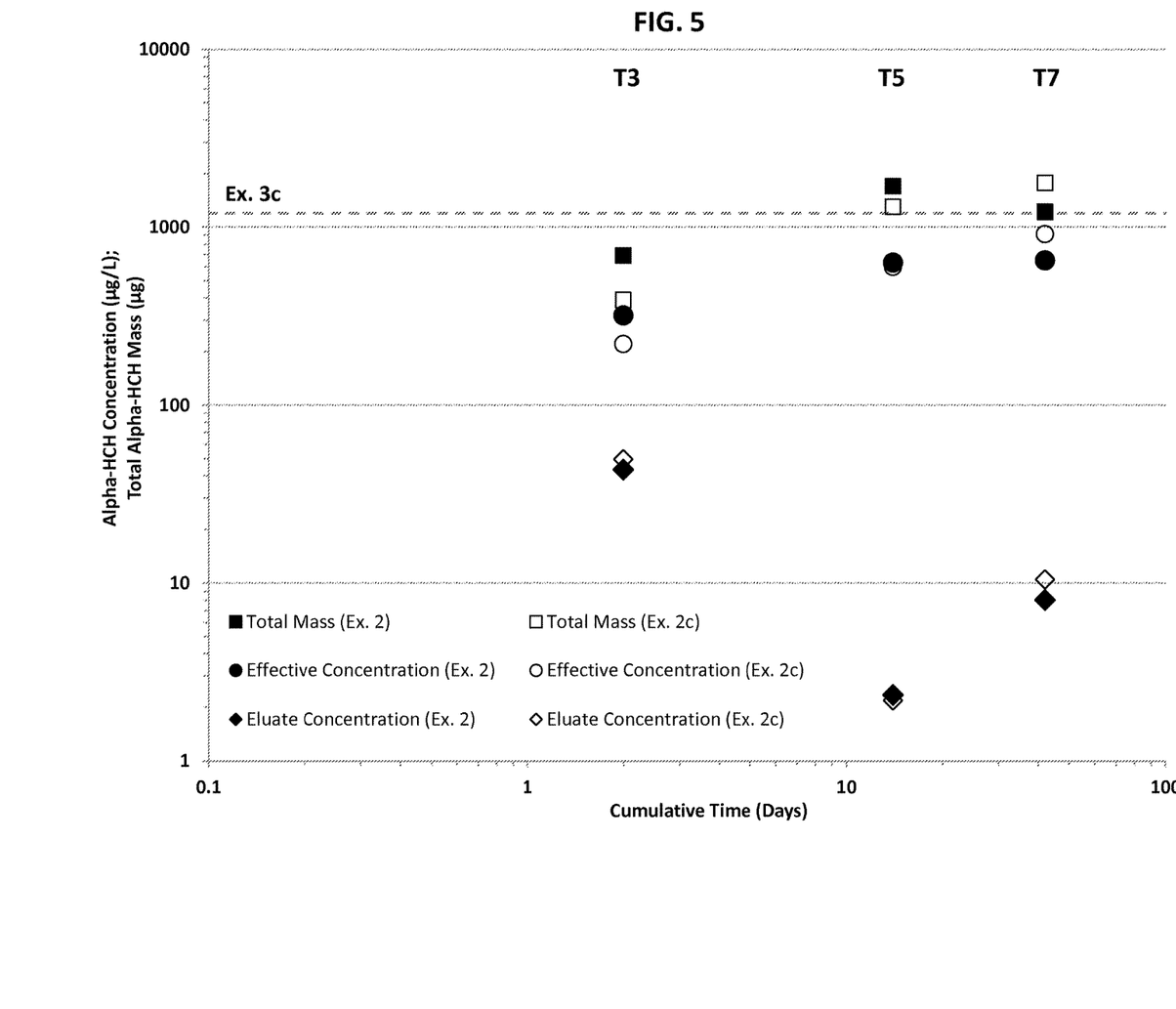
FIG. 5 is a plot of concentration and mass of $\alpha$-HCH as a function of time for an SDL test carried out according to the invention.

The results of the analysis are shown in a log plot in FIG. 5.

The jars and lids used for the tests were washed for reuse in subsequent leach testing.

Example 2C

The test protocol of Example 2 above was repeated using six Control Devices (CDs) wherein a sample was situated in a CD, water added, and the jar capped. After the designated leaching interval, Eluate Concentration and Effective Concentration of α-HCH were determined as in Example 2. The results for the CDs are shown on the log plot of FIG. 5.

The CDs were disposed of after testing was concluded.

Example 3C

A homogenized pesticide-impacted lagoon sample, as used to prepare the cement samples employed in Example 2 and Control Example 2, was used as-received. The homogenized pesticide-impacted lagoon sample was tested for α-HCH using EPA Test Method 1312-20 *Synthetic Precipitation Leaching Procedure* (Revision 0, 1994). The measured amount of α-HCH, 1.2 mg/L, is shown in FIG. 5 and represents the α-HCH concentration leached from the sample by water under the specified leaching test conditions.

Examples 3 and 4

Figure 6:
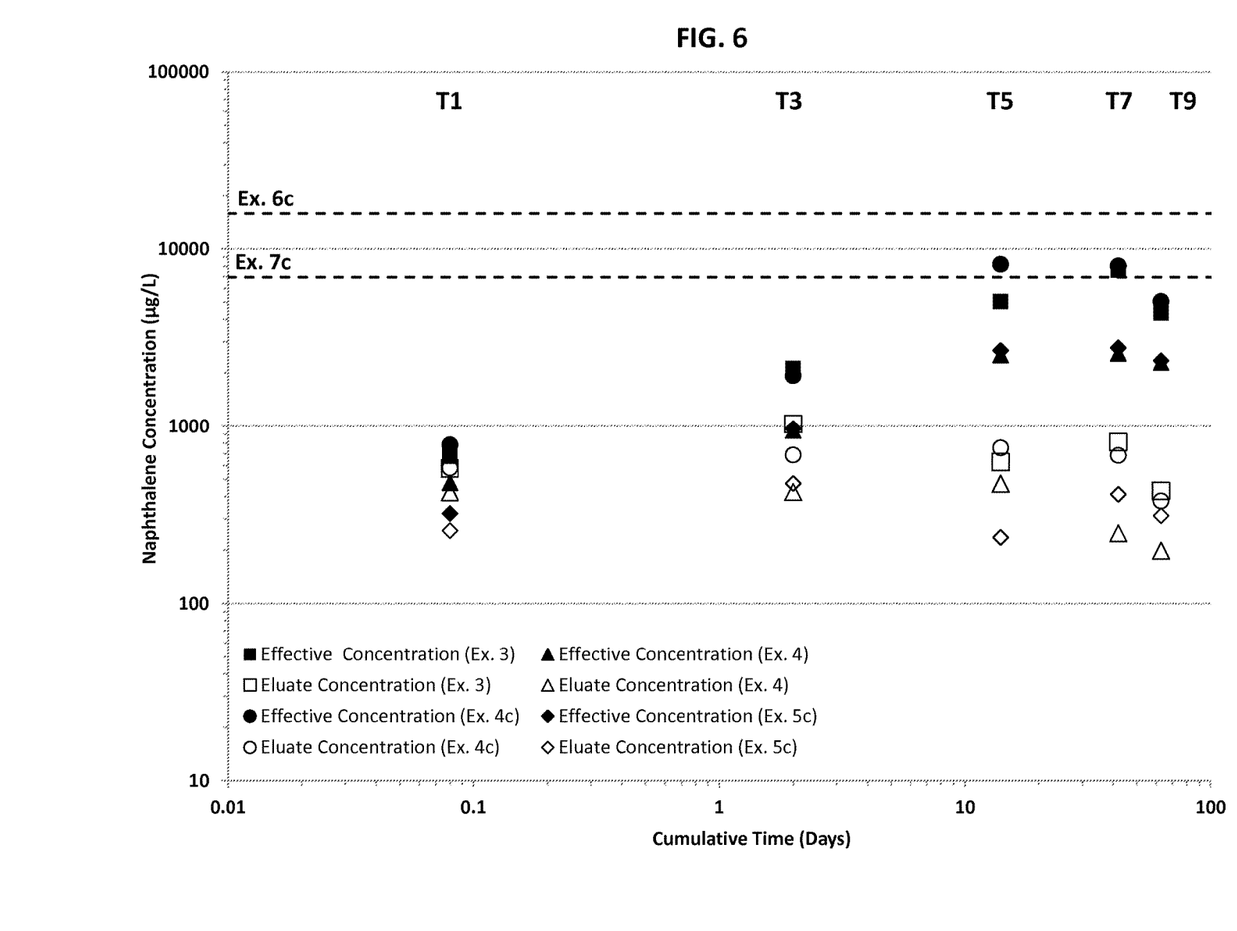
FIG. 6 is a plot of concentration of naphthalene as a function of time for another SDL test of the invention.
Figure 7:
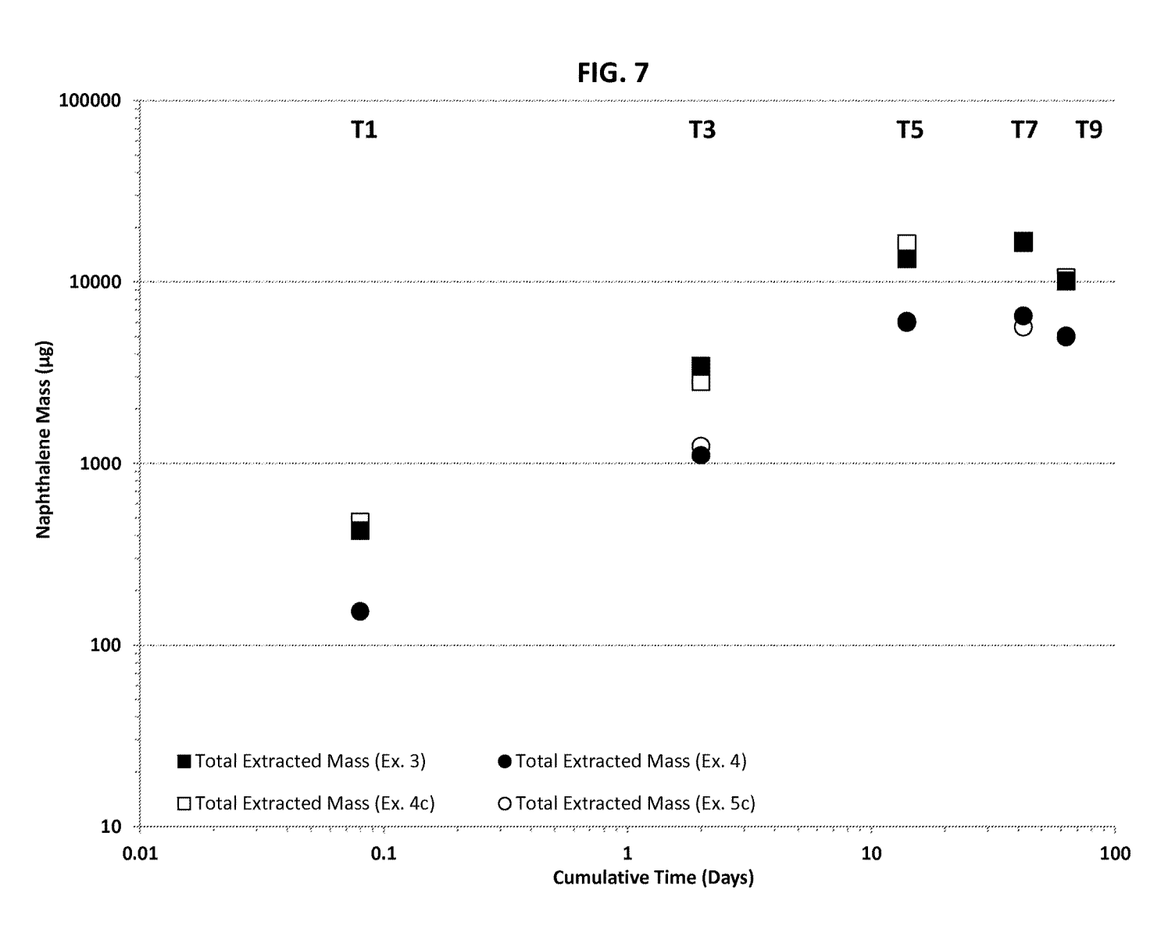
FIG. 7 is a plot of total extracted mass of naphthalene as a function of time for another SDL test of the invention.

The leach testing procedure of Example 2 was repeated with two different homogenized soils heavily impacted with coal tar, Sample A and Sample B. The samples were solidified with cement as in Example 2. The extraction was carried out using the general procedure of Example 2, except that the eluate and acetonitrile extractant were tested for concentration of naphthalene by EPA Method 8270C, *Semivolatile Organic Compounds by Gas Chromatography/Mass Spectrometry (GC/MS)*, Rev. 3, December 1996 for leaching intervals T1, T3, T5, T7, and T9, as shown in Table 1. Sample A was tested as Example 3. Sample B was tested as Example 4. The results of Eluate Concentration and Effective Concentration are shown in FIG. 6. Total Mass is shown in FIG. 7.

Examples 4C and 5C

The test protocol of Examples 3 and 4 was repeated using six CDs, wherein a sample was situated in a CD, and water added and the jar capped. Sample A was used in Example 4C. Sample B was used in Example 5C. After the designated leaching interval, Eluate Concentration and Effective Concentration of naphthalene were determined as in Examples 3 and 4. Results of Eluate Concentration and Effective Concentration are shown in FIG. 6. Total Mass is shown in FIG. 7.

Example 6C

Soil sample A was used as received. The sample was tested for naphthalene using EPA Test Method 1312-20 *Synthetic Precipitation Leaching Procedure* (Revision 0, 1994). The measured amount of naphthalene, 15.9 mg/L, is shown in FIG. 6 and represents the naphthalene concentration leached from the sample by water under the specified leaching test conditions.

Example 7C

The procedure of Example 6C was repeated except using soil sample B as received. The measured amount of naphthalene, 6.96 mg/L, is shown in FIG. 6 and represents the naphthalene concentration leached from the sample by water under the specified leaching test conditions.

Example 5

The leach test protocol from Example 3 was repeated except the test period was T9+7 days, wherein the soil sample A was used. After the leaching period, one of the ID replicates was cut into two pieces, that is, two half-ID sections ($ID_{1/2}$). Each ID and $ID_{1/2}$ was weighed. None of the eluates were analyzed.

The IDs and two $ID_{1/2}$ were extracted with acetonitrile after removal of water and the sample from the jar. In the cases of the $ID_{1/2}$, both of the $ID_{1/2}$ pieces were removed from the original jar and placed in individual fresh jars, such that each $ID_{1/2}$ was extracted separately. Each whole ID and $ID_{1/2}$ was extracted once with 30 mL solvent in a single extraction cycle, wherein the jar was capped and placed on rollers, and rolled for 16 hours at ambient temperature.

The extractants were tested for a number of SVOCs, employing EPA Method 8270C, *Semivolatile Organic Compounds by Gas Chromatography/Mass Spectrometry (GC/MS)*, Rev. 3, December 1996. Previous extractions of IDs employing the combined extractants of four extraction cycles, followed by analysis of Total Mass Absorbed to the PDMS, were used to calculate the extraction efficiency of the IDs for each compound analyzed in this analysis for the whole ID. Using the known extraction efficiency of the ID toward each analyzed compound, the single extraction performed in this Example was analyzed, and the measured amount used to calculate the Total Mass Absorbed to the PDMS. The Total Mass Absorbed of SVOCs acenaphthene (1,2-dihydroacenaphthylene), acenaphthylene, anthracene, fluoranthene, fluorene (9H-fluorene), naphthalene, phenanthrene, and pyrene were thus calculated based on the analysis of a single 30 mL extraction.

The Total Mass Absorbed was used to calculate the μg of each SVOC compound per gram of PDMS (μg analyte/g PDMS) based on the following known constants: for each ID, fiberglass density equals 1.92 g/100 cm$^2$; One ID major surface area equals 556.45 cm$^2$; one fiberglass sheet employed in an ID equals 10.68 g. The μg SVOC/g PDMS values for the whole and $ID_{1/2}$ samples are reported in Table 2. The μg SVOC/g PDMS for the full ID and $ID_{1/2}$ sections were then compared for reproducibility. The differences between the μg SVOC/g PDMS for the whole IDs and the $ID_{1/2}$ sections was determined as a relative percent difference between their average calculated μg SVOC/g PDMS values. The differences between the μg SVOC/g PDMS for the whole IDs compared to the $ID_{1/2}$ sections was also determined as a relative percent difference between their average calculated μg SVOC/g PDMS values. These differences are also reported in Table 2.

TABLE 2

Results of the analysis of soil sample A, analyzed as described in Example 5.

| SVOC | ID, µg/g PDMS | ID$_{1/2}$ (1), µg/g PDMS | ID$_{1/2}$ (2), µg/g PDMS | % Diff., ID: ID$_{1/2}$(avg) | % Diff., ID$_{1/2}$ (1): ID$_{1/2}$ (2) |
|---|---|---|---|---|---|
| acenaphthene | 12.3 | 11.7 | 13.3 | 2 | 13 |
| acenaphthylene | 1.78 | 1.81 | 1.95 | 6 | 8 |
| anthracene | 2.71 | 2.38 | 2.74 | 6 | 14 |
| fluoranthene | 2.52 | 2.08 | 2.23 | 15 | 7 |
| fluorene | 8.21 | 8.70 | 9.56 | 11 | 9 |
| naphthalene | 176 | 194 | 187 | 8 | 4 |
| phenanthrene | 17.5 | 17.0 | 19.0 | 3 | 11 |
| pyrene | 1.82 | 1.47 | 1.48 | 21 | 1 |

Example 6

The leach test, extractions, and calculations of Example 5 were repeated, except that soil sample B was employed in the analysis, the extraction was done with methanol instead of acetonitrile, and the analysis was carried out for the following VOCs: total petroleum hydrocarbons in the gasoline range (TPH-Gasoline), benzene, ethylbenzene, m,p-xylene, o-xylene, and toluene by EPA Method 8260B, *Volatile Organic Compounds by Gas Chromatography/Mass Spectrometry* (*GC/MS*), Rev. 2, December 1996. The results are shown in Table 3.

TABLE 3

Results of the analysis of soil sample B, analyzed as described in Example 6.

| VOC | ID, µg/g PDMS | ID$_{1/2}$ (1), µg/g PDMS | ID$_{1/2}$ (2), µg/g PDMS | % Diff., ID: ID$_{1/2}$(avg) | % Diff., ID$_{1/2}$ (1): ID$_{1/2}$ (2) |
|---|---|---|---|---|---|
| TPH-gasoline | 224 | 203 | 318 | 15 | 44 |
| benzene | 0.09 | 0.05 | 0.04 | 71 | 7 |
| ethylbenzene | 9.30 | 10.1 | 9.82 | 7 | 3 |
| m,p-xylene | 39.2 | 40.4 | 48.2 | 12 | 18 |
| o-xylene | 18.6 | 19.0 | 18.4 | 0 | 4 |
| toluene | 0.65 | 0.39 | 0.37 | 51 | 6 |

Although the present disclosure provides references to preferred embodiments, persons skilled in the art will recognize that changes may be made in form and detail without departing from the spirit and scope of the invention.

What is claimed is:

1. A semi-dynamic leach test device comprising
   a container having a floor, one or more substantially vertical walls defining an opening at the top thereof, the opening having a first width, and a lid designed to removably fasten to the opening; and
   an insert device having a second width and comprising a support and an absorptive polymer disposed on the support and characterized by a sheet-like form having a first and second major side,
   wherein one major side of the insert device is removably arranged between the opening and the lid, and
   the second width is greater than the first width.

2. The device of claim 1 wherein the support is a film, porous film, perforated film, sheet, expanded sheet, perforated sheeting, mesh, scrim, screen, woven fabric, or nonwoven fabric.

3. The device of claim 1 wherein the support comprises a natural or synthetic polymer, metal, fiberglass, or mixture of two or more thereof.

4. The device of claim 1 wherein the support is fiberglass fabric.

5. The device of claim 1 wherein the absorptive polymer comprises a polydiorganosiloxane, polyolefin, a block copolymer of styrene and butadiene, a hydrophobic acrylate polymer, a butyl rubber, a styrene-butadiene rubber, an ethylene-propylene-diene rubber, or a mixture of two or more thereof.

6. The device of claim 1 further comprising a test sample and water.

7. The device of claim 6 wherein the test sample is substantially immersed in the water, the lid is fastened to the opening, and the insert device is disposed between the opening and the lid under conditions wherein substantially no headspace is provided between the water and the insert device.

8. The device of claim 6 wherein the test sample comprises a semi-solid material.

9. The device of claim 6 wherein the insert device is substantially immersed in the water.

10. The device of claim 6 wherein the test sample comprises a solid material.

11. The device of claim 10 wherein the solid material is a monolithic or a compacted granular material.

12. The device of claim 1 wherein the insert device comprises a selected portion of a web, wherein the selected portion consists of a selected width and length.

13. The device of claim 1 wherein the container has a substantially rectangular shape.

14. The device of claim 1 wherein the container has a substantially cylindrical shape.

15. The device of claim 14 wherein the vertical wall is an inner cylindrical wall.

16. The device of claim 15 wherein one major side of the insert device is disposed substantially in contact with the inner cylindrical wall.

17. The device of claim 14 further comprising one or more of a stage, a sample cup, a brace, a string, and a harness.

18. The device of claim 1 wherein the container is a glass jar.

* * * * *